United States Patent [19]

Weber et al.

[11] Patent Number: 5,093,525

[45] Date of Patent: Mar. 3, 1992

[54] N,N'-DISUBSTITUTED GUANIDINES AND THEIR USE AS EXCITATORY AMINO ACID ANTAGONISTS

[75] Inventors: Eckard Weber, Laguna Beach, Calif.; John F. W. Keana, Eugene, Oreg.

[73] Assignees: State of Oregon, acting by and through the Oregon State Board of Higher Education, acting for and on behalf of the Oregon Health Sciences University, Portland; University of Oregon, Eugene, both of Oreg.

[21] Appl. No.: 487,033

[22] Filed: Mar. 2, 1990

Related U.S. Application Data

[63] Continuation-in-part of Ser. No. 237,367, Aug. 29, 1988, which is a continuation-in-part of PCT/US87/01545 Jun. 26, 1987, which is a continuation-in-part of Ser. No. 884,150, Jul. 10, 1986.

[51] Int. Cl.$^5$ .................................. C07C 277/00
[52] U.S. Cl. .................................. 564/238; 564/239
[58] Field of Search .................. 564/238, 239, 634; 514/634

[56] References Cited

U.S. PATENT DOCUMENTS

| | | | |
|---|---|---|---|
| 1,422,506 | 7/1922 | Weiss | 564/238 |
| 1,597,233 | 8/1926 | Heuser et al. | 564/238 |
| 1,642,180 | 9/1927 | Scott | 564/238 |
| 1,672,431 | 6/1928 | Schotte | 564/238 |
| 1,677,235 | 7/1928 | Heuser | 564/238 |
| 2,362,915 | 11/1944 | Hutchinson et al. | |
| 2,633,474 | 3/1953 | Beaver | |
| 3,320,229 | 5/1967 | Szabo et al. | |
| 3,479,437 | 11/1969 | Szabo et al. | |
| 3,976,643 | 8/1976 | Diamond et al. | |
| 4,709,094 | 3/1990 | Weber et al. | |
| 4,906,779 | 3/1990 | Weber et al. | |

FOREIGN PATENT DOCUMENTS 2609534 9/1976 Fed. Rep. of Germany.

OTHER PUBLICATIONS

Keana, J. F. W. et al., *Proc. Natl. Acad. Sci. (USA)* 86 5631–5635 (1989).
Galvin et al., *Biol. Abstr.* 69: 52486 (1980).
Hall et al., *Biol. Abstr.* 70: 39405 (1980).
Kranz et al., *Biol. Abstr.* 70: 80555 (1980).
International Search Report for PCT/US91/01448.

*Primary Examiner*—Paul J. Killos
*Attorney, Agent, or Firm*—Sterne, Kessler, Goldstein & Fox

[57] ABSTRACT

Disubstituted guanidines, e.g., bis-1,3-(o-isopropylphenyl)guanidine, bis-1,3-(m-isopropylphenyl)guanidine, bis-1,3-(1-naphthyl)guanidine, bis-1,3-(m-methoxyphenyl)guanidine, N-(1-naphthyl)-N'-(o-iodophenyl)guanidine, N-(1-naphthyl)-N'-(m-ethylphenyl)guanidine, and N-(1-napthyl)-N'-(o-isoproylphenyl) guanidine, exhibit a high binding affinity to phencyclidine (PCP) receptors. These N,N'-disubstituted guanidine derivatives act as non-competitive inhibitors of glutamate-induced responses generated via the NMDA receptor by acting as blockers for the ion channel of the NMDA receptor-ion channel complex. These compounds thus exert a neuroprotective property and are useful in the therapeutic treatment of neuronal loss in hypoxia, hypoglycemia, brain or spinal chord ischemia, brain or spinal cord trauma, as well as being useful for the treatmnet of epilepsy, Alzheimer's disease, Amyotrophic Laterla Scherosis, Huntington's disease, Down's Syndrome, Korsakoff's disease and other neurodegenerative disorders.

51 Claims, 1 Drawing Sheet

N,N'-DISUBSTITUTED GUANIDINES AND THEIR USE AS EXCITATORY AMINO ACID ANTAGONISTS

STATEMENT AS TO RIGHTS TO INVENTIONS MADE UNDER FEDERALLY SPONSORED RESEARCH AND DEVELOPMENT

This invention was made with government support under Grant Nos MH 42068 and MH 40303 awarded by the National Institutes of Health. The government has certain rights in the invention.

CROSS REFERENCE TO RELATED APPLICATIONS

This application is a continuation-in-part of U.S. application Ser. No. 07/237,367 filed Aug. 29, 1988, which is a continuation-in-part of PCT/US87/01545 filed June 26, 1987 (and its U.S. counterpart), which is a continuation-in-part of U.S. application Ser. No. 06/884,150 filed July 10, 1986.

FIELD OF THE INVENTION

This invention is in the field of medicinal chemistry. In particular, this invention relates to N,N'-disubstituted guanidine analogues, and to compounds and pharmaceutical composition comprising the same, which possess neuroprotective capability. This invention further relates to methods involving the use of N,N'-disubstituted guanidines as excitatory amino acid antagonists, e.g., for treating diseases of the nervous system in which the pathophysiology of the disease involves excessive excitation of nerve cells by agonists of the N-methyl-d-aspartate (NMDA) receptor. Such excessive excitation can lead to dysfunction of the nervous system in the case of epilepsy and to nerve cell degeneration in cases of hypoxia, hypoglycemia, brain or spinal chord ischemia, brain or spinal chord trauma and in neurodegenerative diseases such as Huntington s disease, Amyotrophic Lateral Sclerosis (ALS), Alzheimer's disease, Down's Syndrome and Korsakoff's disease.

BACKGROUND OF THE INVENTION

A wide variety of substituted guanidines are disclosed in the patent literature. For example:
1,411,731 and 1,422,506 discloses diphenylguanidine as a rubber accelerator;
1,597,233 discloses N-o-tolyl-N'-phenyl-guanidine as a rubber accelerator;
1,672,431 discloses N,N'-di-o-methoxyphenyl-guanidine as being useful for therapeutic purposes, especially in the form of water-soluble salts;
1,730,338 discloses N-p-dimethyl-amino-phenyl-N'-phenylguanidine as a rubber accelerator;
1,795,738 discloses a process for the production of N,N'-dialkyl-di-substituted guanidines, including N-di-ethyl-N'-phenyl-guanidine, N-diethyl-N-isoamyl-guanidine, N-dimethyl-N'-isoamylguanidine and N-dimethyl-N'-ethylguanidine;
1,850,682 discloses a process for the preparation of di-substituted guanidine rubber accelerators bearing an additional substituent on the imine nitrogen atom;
2,145,214 discloses the use of disubstituted guanidines, e.g., diarylguanidines especially dixylylguanidine, as parasiticides;
2,254,009 discloses sym-di-2-octyl-guanidine and 2,274,476 and 2,289,542 disclose sym-dicyclohexyl-guanidine as insecticides and moth larvae repellents;
2,633,474 discloses 1,3-bis(o-ethylphenyl)guanidine and 1,3-bis(p-ethylphenyl)guanidine as rubber accelerators;
3,117,994 discloses N,N',N"-trisubstituted guanidines and their salts as bacteriostatic compounds;
3,140,231 discloses N-methyl- and N-ethyl-N'-octyl-guanidines and their salts as antihypertensive agents;
3,248,246 describes (Example 5) a 1,3-disubstituted guanidine whose substituents are hydrophobic hydrocarbon groups, one of which is naphthylmethyl and the other is n-butyl;
3,252,816 discloses various N-substituted and unsubstituted cinnamyl-guanidines and generically the corresponding N'- and N"-alkyl substituted compounds and their salts as antihypertensive agents;
3,270,054 discloses N-2-adamant-1-yl- and N-2-homoadamant-1-yl-oxy-ethyl-thioethyl- and aminoethylguanidine derivatives bearing at most two lower alkyl groups on the N'- and/or N"-nitrogen atom as sympathicolytic and anti-viral agents;
3,301,755 discloses N-ethylenically unsubstituted alkyl-guanidines and the corresponding N'- and/or N"-lower alkyl compounds as hypoglycemic and antihypertensive agents;
3,409,669 discloses N-cyclohexylamino-(3,3-dialkylsubstituted-propyl)-guanidines and the corresponding N'-alkyl- and/or N"-alkyl-substituted compounds as hypotensive agents;
3,547,951 discloses 1,3-dioxolan-4-yl-alkyl-substituted guanidines which have anti-hypertensive activity and discloses lower alkyl, including n-butyl, as a possible substituent on the other amino group;
3,639,477 discloses propoxylguanidine compounds as having anorectic properties;
3,681,459; 3,769,427; 3,803,324; 3,908,013; 3,976,787; and 4,014,934 disclose aromatic substituted guanidine derivatives wherein the phenyl ring can contain hydroxy and/or halogen substituents for use in vasoconstrictive therapy;
3,804,898 discloses N-benzylcyclobutenyl and N-benzylcyclobutenyl-alkyl-guanidines and the corresponding N-alkyl and/or N"-alkyl-substituted compounds as hypotensive agents;
3,968,243 discloses N-aralkyl substituted guanidines and the corresponding N'-alkyl-N"-alkyl and N',N'-aralkyl compounds as being useful in the treatment of cardiac arrhythmias;
3,795,533 discloses o-halo-benzylidene-amino-guanidines and their use as anti-depressants for overcoming psychic depression;
4,007,181 discloses various N,N'-disubstituted guanidines substituted on the imine nitrogen atom by a adamantyl as possessing antiarrhythmic and diuretic activities;
4,051,256 discloses N-phenyl- and N-pyridyl-N'-cycloalkyl-guanidines as antiviral agents;
4,052,455 and 4,130,663 disclose styrylamidines, as analgesics agents or for the prevention of blood platelet aggregation;
4,109,014 discloses N-hydroxysubstituted guanidines and the corresponding N-methyl disubstituted guanidines as vasoconstrictor agents;
4,169,154 discloses the use of guanidines in the treatment of depression;

4,393,007 discloses N-substituted and unsubstituted, N-substituted methyl-N'-unsubstituted, monosubstituted and disubstituted-N''-unsubstituted and substituted guanidines as ganglionic blocking agents; and 4,471,137 discloses N,N,N'N''-tetraalkyl guanidines as being sterically hindered bases useful in chemical synthesis.

4,709,094 discloses 1,3-disubstituted-guanidines, e.g., 1-3-dibutyl-guanidine and 1,3 di-o-tolyl-guanidine (DTG), as sigma brain receptor ligands.

For examples of other substituted guanidines, see, e.g., 1,422,506; 1,642,180; 1,756,315; 3,159,676; 3,228,975; 3,248,426; 3,283,003; 3,320,229; 3,479,437; 3,547,951; 3,639,477; 3,784,643; 3,949,089; 3,975,533; 4,060,640 and 4,161,541.

Geluk, H. W., et al., *J. Med. Chem.*, 12,712 (1969) describe the synthesis of a variety of adamantyl disubstituted guanidines as possible antiviral agents, including N,N'-di-(adamantan-1-yl)-guanidine hydrochloride, N-(adamantan-1-yl)-N'-cyclohexyl-guanidine hydrochloride and N-(adamantan-1-yl)-N'-benzyl-guanidine hydrochloride.

The amino acid L-glutamate is widely thought to act as a chemical transmitter substance at excitatory synapses within the central nervous system. Neuronal responses to glutamate are complex and appear to be mediated by at least three different receptor types, i.e., KA, QA and NMDA subtypes, each being named for their relatively specific ligands, i.e., kainic acid, quisaqualic acid and N-methyl-D-aspartic acid, respectively. An amino acid which activates one or more of these receptor types is referred to as an excitatory amino acid (EAA).

The NMDA subtype of excitatory amino acid receptors is activated during normal excitatory synaptic transmission in the brain. Activation of NMDA receptors under normal conditions is responsible for the phenomena of long-term potentiation, a memory-like phenomenon, at excitatory synapses. Excessive excitation of neurons occurs in epileptic seizures and it has been shown that over-activation of NMDA receptors contributes to the pathophysiology of epilepsy.

NMDA receptors are also strongly involved in nerve cell death which occurs following brain or spinal chord ischemia. Upon the occurrence of ischemic brain insults such as stroke, heart attack or traumatic brain injury, an excessive release of endogenous glutamate occurs, resulting in the over-stimulation of NMDA receptors. Associated with the NMDA receptors is an ion channel. The recognition site, i.e., the NMDA receptor, is external to the ion channel. When glutamate interacts with the NMDA receptor, it causes the ion channel to open, thereby permitting a flow of cations across the cell membrane, e.g., $Ca^{2+}$ and $Na^+$ into the cell and $K^+$ out of the cell. It is believed that this flux of ions, especially the influx of $Ca^{2+}$ ions, caused by the interaction of glutamate with the NMDA receptor, plays an important role in nerve cell death See, e.g., Rothman, S. M. and Olney, J. W., *Trends in Neurosci.* 10(7), 299-302 (1987).

Agents which block responses to NMDA receptor activation therefore have therapeutic uses in the treatment of neurological disorders such as epilepsy and also in the prevention of nerve cell death resulting from hypoxia or hypoglycemia or following brain ischemia which occurs during stroke, trauma and heart attack. A number of disorders of the nervous system are associated with neurodegeneration that may be caused by over-activation of NMDA receptors. Antagonists of NMDA receptor-mediated responses have potential therefore for the treatment of such disorders as Alzheimer's disease, Huntington's chorea, Amyotrophic Lateral Sclerosis, Down's Syndrome and Korsakoff's disease.

Research on the NMDA receptor-ion channel complex has led to the determination of a receptor site within the ion channel known as the PCP receptor. See Vincent, J. P., Kartalovski, B., Geneste, P., Kamenka, J. M. and Lazdunski, M., *Proc. Natl. Acad. Sci. U.S.A.* 76. 4678-4682 (1979); Zukin, S. R. and Zukin, R. S., *Proc. Natl. Acad. Sci. U.S.A.* 76. 5372-5376 (1979); Sonders, M. S., Keana, J. F. W. and Weber, E., *Trends in Neurosci.* 11(1), 37-40 (1988); and Anis, N. A., Berry, S. C., Burton, N. R. and Lodge, D., Br. J. Pharmacol. 79, 565-575 (1983). A compound which binds to the PCP receptor can act as an ion-channel blocker, thereby interrupting the flow of ions through the cell wall. In this manner, agents which interact with the PCP receptor act as non-competitive blockers reducing the agonist action of glutamate at the NMDA receptor.

Known PCP receptor ligands include PCP, i.e., phencyclidine, analogues such as 1-[1-(2-thienyl)cyclohexyl]-piperidine (TCP), benzomorphan (sigma) opiates, and (+)-5-methyl-10,11-dihydro-5H-dibenzo[a,d]cycloheptene-5,10-imine (i.e., the drug MK-801, see U.S. Pat. No. 4,399,141). See, also, Wong, E. H. F., Kemp, J. A., Priestly, T., Knight, A. R., Woodruff, G. N., and Iversen, L. L., *Proc. Natl. Acad. Sci. U.S.A.* 83 7104-7108 (1986). MK-801 is apparently the most potent selective PCP receptor ligand/NMDA channel blocker known to date.

We have identified compounds which exhibit a high affinity for binding to the PCP receptor and are structurally different from known PCP receptor ligands.

SUMMARY OF THE INVENTION

It is an object of this invention to provide N,N'-disubstituted guanidines which exhibit a high affinity for the PCP receptor in the NMDA receptor-channel complex.

It is another object of the invention to provide N,N'-disubstituted guanidines to aid in PCP receptor research.

A further object of the invention is to provide N,N'-disubstituted guanidines which are useful for the treatment of neurological conditions such as epilepsy and those nervous system disorders associated with neurodegeneration.

It is a further object of the invention to provide a method for treating diseases of the nervous system associated with excessive excitation of nerve cells by agonists of the NMDA receptor.

It is yet a further object of the invention to treat or prevent dysfunction of the nervous system causing, for example, epilepsy, associated with excessive excitation of nerve cells by agonists of the NMDA receptor by the administration of effective amounts of N,N'-disubstituted guanidine compounds having a high affinity for the PCP receptor.

It is yet a further object of the invention to treat neurodegenerative conditions and/or nerve cell death resulting from hypoxia, hypoglycemia, brain or spinal cord ischemia, brain or spinal chord trauma, and the like, by the administration of effective amounts of N,N'-disubstituted guanidine compounds having a high affinity for the PCP receptor.

It is yet a further object of the present invention to treat neurodegenerative conditions associated with the various neurodegenerative diseases such as Huntington's disease, Amyotrophic Lateral Sclerosis, Alzheimer's disease, Down's Syndrome and Korsakoff's disease by the administration of effective amounts of N,N'-disubstituted guanidines having a high affinity for the PCP receptor.

Upon further study of the specification and appended claims, further objects and advantages of this invention will become apparent to those skilled in the art.

BRIEF DESCRIPTION OF THE DRAWING

Various other objects, features and attendant advantages of the present invention will be more fully appreciated as the same becomes better understood when considered in conjunction with the accompanying Figure wherein.

DESCRIPTION OF THE PREFERRED EMBODIMENTS

The above-mentioned objects have been achieved by the determination of certain N,N'-disubstituted guanidines which exhibit a high binding affinity for the PCP receptor site. Typical symmetrical N,N'-disubstituted guanidines having high binding to the PCP receptor include bis-1,3-(o-isopropylphenyl)guanidine, bis-1,3-(m-isopropylphenyl)guanidine, bis-1,3-(1-naphthyl)-guanidine and bis-1,3-(m-methoxyphenyl)guanidine.

It has also been discovered that certain asymmetrical N,N'-disubstituted guanidines have very high binding to the PCP receptor. The preferred asymmetrical N,N'-disubstituted guanidines of this invention are those of the formula

I wherein R and R' are different and are an alkyl group of at least 4 carbon atoms or carbocyclic aryl groups of at least 6 carbon atoms, e.g., are alkyl of 4 or more carbon atoms, e.g., a 4 to 12 carbon atom, preferably a straight chain, alkyl group and more preferably a 4 to 8 carbon atom alkyl group, for example, butyl, isobutyl, tert-butyl, amyl, hexyl, octyl, nonyl and decyl; cycloalkyl of 3 to 12 carbon atoms, e.g., cyclopropyl, cyclopentyl, cyclohexyl, cyclohexenyl, cycloheptyl, 1,4-methylenecyclohexyl, adamantyl, norbornyl, isobornyl, menthyl, cyclopentylmethyl, cyclohexylmethyl, 1- or 2-cyclohexylethyl and 1-, 2- or 3-cyclohexylpropyl; carbocyclic aryl, alkaryl, aralkyl or heterocyclic, e.g., of 6 to 18 carbon atoms and containing 1-3 separate or fused rings, and 0-5 O, N and/or S ring atoms in an aryl, alicyclic or mixed ring system, e.g., phenyl, benzyl, 1- and 2-phenylethyl, 1-, 2-, or 3-phenylpropyl; o-, m-, or p-tolyl, m,m'-dimethylphenyl, o-, m-, or p-ethylphenyl, m,m'-diethylphenyl, m-methyl-m'-ethylphenyl and o-propylphenyl, naphthyl, 2-naphthyl, biphenyl; indanyl, for example, 4-indanyl; indenyl, for example, 1- or 4-indenyl; indolyl, for example, 7-indolyl; benzthiazole, quinolinyl, pyridyl, pyrimidinyl, pyrazinyl, furanyl, thienyl, pyrrolyl, thiazolyl, oxazolyl, and imidazolyl.

1, 2, 3 or more substituents may be present on the R and R' hydrocarbon groups, e.g., alkyl of 1-8 carbon atoms, e.g., methyl, ethyl; halo, e.g., chloro, bromo, iodo, fluoro; nitro; azido; cyano; isocyanate; amino; lower-alkylamino; di-loweralkylamino; trifluoromethyl; alkoxy of 1-8 carbon atoms, e.g., methoxy, ethoxy and propoxy; acyloxy, e.g., alkanoyloxy of 1-8 carbon atoms, e.g., acetoxy and benzoxy; amido, e.g., acetamido, N-ethylacetamido; carbamido, e.g., carbamyl, N-methylcarbamyl, N,N'-dimethylcarbamyl; etc.

Preferred are compounds of Formula I wherein R and R' each are nonidentical aryl groups, including aryl groups substituted with one or more of the foregoing substituents, for example, in the o-, m- or p-position or the o-, p- or m,m'-position, when the phenyl group is disubstituted.

Especially preferred asymmetrical guanidines include N-(1-naphthyl)-N'-(o-iodophenyl)guanidine, N-(1-naphthyl)-N'-(m-ethylphenyl)guanidine, N-(1-naphthyl)-N'-(o-isopropylphenyl)guanidine, N-(1-naphthyl)-N'-(m-tolyl)guanidine, N-(1-naphthyl)-N'-(o-ethylphenyl)guanidine, N-(1-naphthyl)-N'-(m-isopropylphenyl)guanidine, N-(1-naphthyl)-N'-(m-methoxyphenyl)-guanidine, N-(1-naphthyl)-N -(4-indanyl)guanidine, N-(m-ethylphenyl)-N'-(m-tolyl)guanidine, N-(m-ethylphenyl)-N'-(o-iodophenyl)guanidine, N-(m-ethylphenyl)-N'-(o-ethylphenyl)-guanidine, N-(m-ethylphenyl)-N'-(o-isopropylphenyl)guanidine, N-(m-ethylphenyl)-N'-(m-isopropylphenyl)guanidine, N-(m-ethylphenyl)-N'-(m-methoxyphenyl)guanidine, N-(m-ethylphenyl)-N'-(4-indanyl)guanidine, N-(o-ethylphenyl)-N'-(m-tolyl)guanidine, N-(o-ethylphenyl)-N'-(o-iodophenyl)guanidine, N-(o-ethylphenyl)-N'-(o-isopropylphenyl)guanidine, N-(o-ethylphenyl)-N'-(m-isopropylphenyl)guanidine, N-(o-ethylphenyl)-N'-(m-methoxyphenyl)guanidine, N-(o-ethylphenyl)-N' -(4-indanyl)-guanidine, N-(o-iodophenyl)-N'-(m-tolyl)guanidine, N-)o-iodophenyl)-N'-N'(o-isopropylphenyl)guanidine, N-(o-iodophenyl)-N'-(m-isopropylphenyl)guanidine, N-(o-iodophenyl)-N'-(m-methoxyphenyl)guanidine, N-(o-iodophenyl)-N'-(4-indanyl)guanidine, N-(o-isopropylphenyl)-N'-(m-tolyl)guanidine, N-(o-isopropylphenyl)-N'-(m-isopropylphenyl)guanidine, N-(o-isopropylphenyl)-N'-(m-methoxyphenyl)guanidine, N-(o-isopropylphenyl)-N'-(4-indanyl)guanidine, N-(m-isopropylphenyl)-N'-(m-tolyl)guanidine, N-(m-isopropylphenyl)-N'-(m-methoxyphenyl)guanidine, N-(m-isopropylphenyl)-N'-(4-indanyl)guanidine, N-(m-methoxyphenyl)-N'-(m-tolyl)guanidine, N-(m-methoxyphenyl)-N'-(4-indanyl)guanidine, and N-(4-indanyl)-N'-(m-tolyl)guanidine.

Disubstituted guanidines are the subject of copending application serial no. 07/237,367 filed August 29, 1988, and U.S. Pat. No. 4,709,094, whose disclosures are incorporated herein by reference. The preferred guanidines in U.S. Pat. No. 4,709,094 are described therein by the formula:

wherein R and $R^1$ are each independently alkyl, cycloalkyl, carbocyclic aryl, alkaryl or aralkyl. As a class, these compounds are described in this patent as exhibiting a highly selective binding activity to the sigma brain receptor. DTG itself also exhibits a strong selectivity for the sigma receptor (Weber, E., Sonders, M., Quarum, M., McLean, S., Pou, S. & Keana, J. F. W., *Proc. Natl. Acad. Sci. U.S.A.* 83, 8786-8788 (1986)). In copending application Ser. No. 07/237,367, it is disclosed that additional specific members of this class of disubstituted guanidines exhibit a high binding activity for the PCP receptor. Surprisingly, it has now been discovered that certain asymmetrically substituted guanidines exhibit enhanced binding for the PCP receptor compared to the symmetrically substituted guanidines.

These N,N'-disubstituted guanidines can readily be prepared by conventional chemical reactions, e.g., when R and R' are the same, by reaction of the corresponding amine with cyanogen bromide. Other methods which can be employed include the reaction of an amine with a preformed alkyl or aryl cyanamide. See Safer, S. R., et al., *J. Org. Chem.* 13:924 (1948). This is the method of choice for producing asymmetrical N,N'-disubstituted guanidines. For a recent synthesis of asymmetrical guanidines, see G. J. Durant et al., *J. Med. Chem.* 28:1414 (1985), and C. A. Maryanoff et al., *J. Org. Chem.* 51:1882 (1986), the disclosures of which are incorporated by reference herein.

In a compositional aspect, this invention relates to a pharmaceutical composition in unit dosage form and adapted for systemic administration to a subject, e.g., a human being, comprising per unit dosage an amount of a N,N'-disubstituted guanidine effective to alter the NMDA receptor-modulated activity of the brain, wherein the N,N'-disubstituted guanidine has a high affinity for the PCP receptor.

In another compositional aspect, this invention relates to a neuroprotecting symmetrical N,N'-disubstituted guanidine which exhibits a high binding activity with respect to the PCP receptor in mammalian nerve cells, e.g., bis-1,3-(o-isopropylphenyl)guanidine, bis-1,3-(m-isopropylphenyl)guanidine, bis-1,3-(1-naphthyl)-guanidine and bis 1,3-(m-methoxyphenyl)guanidine, and the physiologically acceptable salts thereof.

In another compositional aspect, this invention relates to a neuroprotecting asymmetrical N,N'-disubstituted guanidine which exhibits a high binding activity with respect to the PCP receptor in mammalian nerve cells, e.g., N-(1-naphthyl)-N'-(o-iodophenyl)guanidine, N-(1-naphthyl)-N'-(m-ethylphenyl)guanidine and N-(1-naphthyl)-N.-(o-isopropylphenyl)guanidine, and the physiologically acceptable salts thereof.

In a method aspect, this invention relates to a method for treating or preventing certain neurological disorders, including the consequences of stroke or traumatic brain injury, epilepsy or neurological diseases comprising the administration of an effective amount of a N,N'-disubstituted guanidine having a high affinity for the PCP receptor to a subject in need of such treatment. Such N,N'-disubstituted guanidines possess utility as non-competitive blockers of NMDA-receptor-mediated effects.

In a further method aspect, this invention relates to a method of ameliorating the neurotoxic effect induced by glutamate interacting with the NMDA receptor of a nerve cell, comprising administering to a subject, e.g., a human being exhibiting symptoms of or susceptible to such neurotoxic effect, a N,N'-disubstituted guanidine having a high affinity for the PCP receptor of the nerve cell in an amount effective to ameliorate the neurotoxic effect. The term "high affinity" means the compound exhibits an equilibrium dissociation constant of about 1 µM or less in a PCP receptor binding assay, typically a PCP receptor assay as described below. More preferably, the compound exhibits an equilibrium dissociation constant of about 500 nM or less in a PCP receptor binding assay, most preferably, the compound exhibits an equilibrium dissociation constant of about 100 nM or less in a PCP receptor binding assay.

In another method aspect, this invention relates to a method of inhibiting NMDA receptor-ion channel related neurotoxicity comprising administering to a mammal a N,N'-disubstituted guanidine possessing a high affinity for the PCP receptor of a nerve cell, in an amount effective to inhibit the neurotoxicity.

In another method aspect, the present invention relates to a method of treating Korsakoff's disease, a chronic alcoholism-induced condition, comprising administering to a mammal a N,N'-disubstituted guanidine possessing a high affinity for the PCP receptor of a nerve cell, in an amount effective to treat the disease. Pretreatment of animals with the NMDA antagonist MK-801 markedly attenuates the extent of cell loss, hemorrhages and amino acid changes in a rat model of Korsakoff's disease. See Langlais, P. J. et al., *Soc. Neurosci. Abstr.* 14:774 (1988). Therefore, the N,N'-disubstituted guanidines of the present invention have utility for the attenuation of cell loss, hemorrhages and amino acid changes associated with Korsakoff's disease.

Such N,N'-disubstituted guanidines and other non-competitive blockers of NMDA receptor-mediated responses can be determined by a method involving: (a) determining the binding affinity with respect to the PCP receptor by competitive displacement of tritiated MK-801; (b) in vitro cytotoxicity studies measuring the ability of the compound to prevent nerve cell death caused by exposure to glutamate; and (c) determination of in vivo neuroprotective ability using animal models.

Evaluation of the binding activity of organic compounds with respect to the PCP receptor is performed using radioligand binding assays. The compounds are tested to determine their ability to displace tritiated-MK-801 which is used to label PCP receptors. Evaluating the competitive displacement binding data, the preferred compounds are those which exhibit a high affinity (i.e., low $IC_{50}$ value) for the PCP receptors.

Under the binding activity studies an $IC_{50}$ value of at most about 1 µM, preferably at most about 500 nM, most preferably, at most about 100 nM, indicates a high binding affinity.

In the neurotoxicity studies cultured mammalian neurons or cell lines expressing EAA receptors are exposed in vitro to glutamate and the compound under investigation. The amount of an enzyme, lactate dehydrogenase (LDH), released from the cells into the medium is a measure of cell death. This in vitro cell death assay is described in greater detail below.

In the in vivo neurotoxicity studies, the experimental model of McDonald, J. W., et al.. (In: *Sigma and Phencyclidine-like Compounds as Molecular Probes in Biology*, Ed. Domino, E. F., and Kamenka, J. -M., pp. 697-707 (1988), NPP Books, Ann Arbor, Mich.) can be employed. In this model, an NMDA injection into one cerebral hemisphere of a rat pup causes brain injury which resembles the lesion produced by hypoxia-ischemia. The ability of test compounds to limit the NMDA-induced lesion is a measure of their neuroprotective properties; and, since the compounds are administered intraperitoneally, the model also provides information about a compound's ability to cross the blood-brain barrier.

The compounds of this invention can be administered intranasally, orally or by injection, e.g., intramuscular, intraperitoneal or intravenous injection or by transdermal, intraoccular or enteral means. The optimal dose can be determined by conventional means. Because many of the N,N'-disubstituted guanidines employed in this invention are substantially water insoluble, they are ordinarily administered in the protonated form, e.g., as a pharmaceutically acceptable salt of an organic or inorganic acid, e.g., hydrochloride, sulfate, hemi-sulfate, phosphate, nitrate, acetate, oxalate, citrate, malate, etc.

The compounds of this invention can be employed in mixture with conventional excipients, i.e., pharmaceutically acceptable organic or inorganic carrier substances suitable for parenteral, enteral or intranasal application which do not deleteriously react to the active compounds. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or a carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Intravenous or parenteral administration, e.g., subcutaneous, intraperitoneal, or intramuscular are preferred. The compounds of this invention being particularly valuable in the treatment of mammalian subjects, e.g., humans, wherein the pathophysiology of the disease involves excessive excitation of nerve cells by agonists of the NMDA receptor. Typically, such subjects include those suffering from or likely to suffer from nervous system dysfunctions resulting from, for example, epilepsy or nerve cell degeneration which is the result of hypoxia, hypoglycemia, brain or spinal chord trauma, or brain or spinal chord ischemia. Typical candidates for treatment include heart attack, stroke, brain or spinal cord injury patients, patients undergoing major surgery where brain ischemia is a potential complication and patients [divers] suffering from decompression sickness due to gas emboli in the blood stream. Other candidates for treatment include those patients afflicted with neurodegenerative diseases such as Huntington's disease, Amyotrophic Lateral Sclerosis, Alzheimer's disease, Down's Syndrome and Korsakoff's disease.

It will be appreciated that the actually preferred amounts of active compounds used will vary according to the specific compound being utilized, the particular compositions formulated, the mode of application and the particular site of administration. Optimal administration rates for a given protocol of administration can be readily ascertained by those skilled in the art using conventional dosage determination tests conducted with regard to the foregoing guidelines.

Like the guanidines of U.S. Pat. Nos. 1,411,713, 1,422,506 and 1,597,233, the N,N'-disubstituted guanidines of the present invention may also be used as rubber accelerators.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire text of all applications, patents and publications cited above and below are hereby incorporated by reference.

EXAMPLES

In the examples below, melting points were determined in open capillary tubes on a Thomas-Hoover apparatus (compounds melting $<230°$ C.) or on a Melt-Temp (compounds melting $>230°$ C.) and are uncorrected. The NMR spectra of all compounds were recorded on a General Electric QE-300, and chemical shifts are reported in ppm relative to the residual signal of the deuterated solvent ($CHCl_3$, 7.26 ppm; $HCD_2OD$, 3.30 ppm). IR spectra were recorded on a Nicolet 5DXB FT-IR, or on a Perkin-Elmer model 1420 in $CHCl_3$ or neat. IR and NMR spectra of all compounds are consistent with their assigned structures. Elemental analyses were performed by Desert Analytics (Tucson, Ariz.), or Galbraith Laboratories (Knoxville, Tenn.). N,N-Dimethyl-1-naphthylamine, 3-ethylaniline, N-ethyl-N-1-naphthylamine, BrCN, $CH_3I$, 6-bromohexanoyl chloride, and butyllithium (2.5M) were obtained from Aldrich Chemical Co. and used as received. o-Isopropylanaline and o-toluidine were obtained from Aldrich and freshly distilled by bulb to bulb distillation at reduced pressure. Dimethyl formamide and triethylamine were stirred in $CaSO_4$, distilled under reduced pressure, and stored over molecular sieves. Chlorobenzene was freshly distilled from $CaH_2$. Ether and tetrahydrofuran were refluxed over sodium benzophenone, and freshly distilled under $N_2$. All other solvents were reagent grade.

EXAMPLE 1

Preparation of N,N'-di-(o-isoprooylphenyl)guanidine (Compound II)

o-Isopropyl aniline (2.00 g. 14.8 mmol) in absolute ethanol (8 ml) was added to a stirred solution of cyanogen bromide (0.716 g, 6.76 mmol) in absolute ethanol (3 ml). The reaction mixture was heated to 150° C. under a rapid stream of $N_2$ for 40 min. in an open vessel while allowing ethanol to escape. After cooling to 25° C., the resulting glassy solid was dissolved in $CH_2Cl_2$ (15 ml). This solution was extracted with 1N HCl (3×15 ml). The aqueous layer was basified with an excess of NaOH to provide a white precipitate (0.3 g, 5.5%). This precipitate was filtered off and crystallized in $EtOH/H_2O$ (1:1) to provide the title compound (80.2 mg, 1.5%) as white needles. mp 175.5°–177° C. (dec).

IR (CHCl$_3$): 1640, 3400, 3500 cm$^{-1}$ $^1$H NMR: δ 1.221 (d, 6 H), 3.303 (m, 3 H), 7.123–7.293 (m, 4 H)

$^{13}$C NMR: 23.412, 28.083, 38.701, 126.395, 126.677

Anal. Calcd for C$_{19}$H$_{25}$N$_3$: C, 77.25; H, 8.53; N, 14.22. Found: C, 77.25; H, 8.50; N, 14.09.

EXAMPLE 2

Preparation of N,N'-di-(m-isoprooylphenyl)guanidine (Compound III)

A solution of cyanogen bromide (0.5 g, 4.73 mmol) and m-isopropylaniline[1] (1.28 g, 9.46 mmol) in 95% EtOH (8 ml) was heated at 70°–80° C. for 2.5 hours. The reaction was allowed to cool to room temperature and diluted with 95% EtOH (8 ml). 10% NaOH solution was added and the resulting white precipitate was filtered off and recrystallized from 95% EtOH-H$_2$O to give N,N'-di-(m-isopropylphenyl)guanidine as white needles (590 mg, 21.5%). mp 118°–119° C.

[1] Nitya Anand et al., *Ind. J. Chem.* 19B, 873 (1980).

IR (CHCl$_3$): 1650, 3400, 3500 cm-1

$^1$H NMR (CD$_3$OD): δ 1.25 (d, 12 H, J=7.5 Hz), 2.75 –2.95 (m, 2 H), 6.88 (d, 2 H, J=7.5 Hz), 6.98-7.10 (m, 4 H), 7.18 (t, 2 H, 7.5 Hz).

Anal. Calcd for C$_{19}$H$_{25}$N$_3$: C, 77.25; H, 8.53; N, 14.22. Found: C, 77.28; H, 8.47; N, 14.23.

EXAMPLE 3

Preparation of N,N'-di-(1-naphthyl)guanidine (Compound IV)

A solution of cyanogen bromide (1.2 g, 11.32 mmol) in ethanol (2 ml) was syringed into a stirred solution of 1-aminonaphthalene (3.11 g, 21.37 mmol) in ethanol (20 ml) under N$_2$ over 10 min and then continued stirring for 3 days. The reaction mixture was then fused at 150° C. for 5 hours (while allowing ethanol to escape) to give a yellow solid. It was then taken up in hot ethanol (25 ml) and the insoluble residue was filtered off. The soluble portion was basified with 1N NaOH solution (20 ml) and the resulting solid was filtered to give a brownish solid (1.887 g.). It was recrystallized twice from absolute ethanol to give the title compound (207 mg, 6.2%) as white needles. mp 210°–211° C. Lit mp 197-198.5[2]

[2] Naunton, W. J. trans. Inst. Rubber Industry 2, 147-166 (1926).

IR (KBr): 1643 cm$^{-1}$ $^1$H NMR (CDCl$_3$): δ 4.540 (br, NH), 7.296-8.00 (m, 14 H).

$^{13}$C NMR (CDCl$_3$): δ 123.236, 124.596, 125.948, 126.002, 128.141, 150.468.

Anal. Calcd for C$_{21}$H$_{25}$N$_3$: C, 81.01; H, 5.50; N, 13.49. Found: C, 81.28; H, 5.54; N, 13.45.

EXAMPLE 4

Preparation of N,N'-di-(m-methoxyphenyl)guanidine (Compound V)

m-Anisidine (2.1 g, 17.1 mmol) and cyanogen bromide (923 mg, 8.71 mmol) in 95% EtOH (10 ml) was heated at 75°–85° C. for 10 hours and then allowed to cool to room temperature. The reaction mixture was then partitioned between dichloromethane and 10% NaOH solution. The organic layer was concentrated and the resulting residue was recrystallized from 95% EtOH to give the title compound (1.31 g, 55%) as white needles. mp 134°–135° C.

IR (CHCl$_3$): 1650, 3400, 3500 cm$^{-1}$.

$^1$H NMR (CDCl$_3$): δ 3.672 (s, 6H), 6.61 (dd, 2H, J=7.93 and 1.6 Hz), 6.67-6.71 (m, 4H), 7.21 (t, 1H, J=7.96 Hz).

Anal. Calcd for C$_{15}$H$_{17}$N$_3$O$_2$: C, 66.34; H, 6.32; N, 15.49. Found: C, 66.17; H, 6.32; N, 15.35.

EXAMPLE 5

Preparation of N-(1-naphthyl)-N'-(o-iodophenyl)guanidine (Compound VI)

a. 1-Naphthylcyanamide. A solution of cyanogen bromide (670 mg, 6.34 mmol) in Et$_2$O (15 ml) was added to a stirred solution of 1-aminonaphthalene (1.45 g, 10.12 mmol) in Et$_2$O (40 ml) at room temperature and then heated at 45°–50° C. for 5 hours. The reaction was allowed to cool to room temperature and the aminonaphthalene hydrobromide was filtered off and the filtrate was washed with H$_2$O (2×20 ml). Evaporation of the Et$_2$O layer, and recrystallization of the resulting off-white residue from 95% EtOH gave 1-naphthylcyanamide (350 mg, 28.8%) as light cream needles. mp 132°–133° C. IR (CHCl$_3$): 2240, 3405 cm$^{-1}$.

b. A solution of 1-naphthylcyanamide (182 mg, 1.08 mmol) and o-iodophenylaniline hydrochloride (279 mg, 1.09 mmol) in chlorobenzene (5 ml) was heated at 135°–140° C. for 14 hours. It was concentrated and the residue was partitioned between dichloromethane and 10% NaOH solution. The organic layer was dried over Na$_2$SO$_4$ and concentrated. The resulting light green residue was recrystallized from 95% EtOH-H$_2$O to give N-(1-naphthyl)-N'-(o-iodophenyl)-guanidine (140 mg, 33%) as off-white needles. mp 154°–155° C.

IR (CHCl$_3$): 1650, 3400, 3500 cm$^{-1}$.

$^1$H NMR (CDCl$_3$): δ 6.80 (t, 1H, J=7.25 Hz), 7.26-7.54 (m, 7 H), 7.70 (d, 1H, J=7.2 Hz), 7.84-7.91 (m, 2H), 8.15-8.23 (m, 1H)

Anal. Calcd for C$_{17}$H$_{14}$N$_3$I: C, 52.76; H, 3.65; N, 10.86. Found: C, 52.54; H, 3.54; N, 10.86.

EXAMPLE 6

Preparation of N-(1-naphthyl)-N'-(m-ethylphenyl)guanidine (Compound VII)

a. m-Ethylphenylcyanamide. A solution of cyanogen bromide (3.31 g, 31.26 mmol) in Et$_2$O (25 ml) was added slowly to a stirred solution of m-ethylaniline (6.06 g, 50 mmol) in Et$_2$O (50 ml) and continued stirring at room temperature for 6 hours. A white precipitate of m-ethylaniline hydrobromide (4.46 g) was filtered off, and the filtrate was washed with H$_2$O (2×20 ml). Evaporation of the ether layer afforded m-ethylphenylcyanamide (3.85 g, 96.5%) as a thick liquid. IR (film): 2225 cm$^{-1}$.

b. A solution of m-ethylphenylcyanamide (730 mg, 2.99 mmol) and 1-naphthylamine hydrochloride (900 mg, 5.05 mmol) in chlorobenzene (20 ml) was heated at 140°–145° C. for 12 hours. It was allowed to cool to room temperature, concentrated and the residue was partitioned between dichloromethane and 10% NaOH solution. The organic layer was concentrated and the resulting residue was recrystallized from abs. EtOH-H$_2$O to give N-(1-naphthyl)-N'-(m-ethylphenyl)guanidine (55 mg, 4%) as off-white needles. mp 96°–98° C.

IR (CHCl$_3$): 1650, 3400, 3500 cm$^{-1}$.

$^1$H NMR (CDCl$_3$): δ 1.16 (t, 3H, J=9 Hz), 2.55 (q, 2H, J=9 Hz), 4.83 (br, NH), 6.89-8.20 (m, 11H)

Anal. Calcd for $C_{19}H_{19}N_3$: C, 78.85; H, 6.62; N, 14.52. Found: C, 79.35; H, 6.61; N, 14.32.

EXAMPLE 7

Preparation of
N-(1-naphthyl)-N'-(o-isopropylphenyl)guanidine
(Compound VIII)

a. o-Isopropylphenylcyanamide. A solution of cyanogen bromide (3.79 g, 35.8 mmol) in ether (50 ml) was added slowly to a stirred solution of o-isopropylaniline (7.75 g, 57.3 mmol) in ether (150 ml) and then heated to reflux at 45° C. for 2.5 hours and at room temperature for 6 hours. A white precipitate of o-isopropylaniline hydrobromide was filtered off, and the filtrate was washed with water (2×20 ml) and dried over $Na_2SO_4$. It was filtered and concentrated and the residue was purified by flash chromatography on $Si_2O$ to give o-isopropylphenylcyanamide (2.5 g, 27%) as very light yellow crystals. mp 75°-77° C.

IR ($CHCl_3$): 2230, 3410 cm$^{-1}$.

b. A solution of o-isopropylphenylcyanamide (1.13 g, 7.05 mmol), 1-naphthylamine hydrochloride (1.1 g, 7.04 mmol) and 1-aminonaphthalene (14.38 mg, 0.1 mmol) in chlorobenzene (20 ml) was heated to 150° C. for 4 hours and at room temperature for 10 hours. It was concentrated and the residue was partitioned between dichloromethane and 10% NaOH solution. The organic layer was concentrated and the resulting solid was recrystallized from EtOH - $H_2O$ (10:1) to give N-(1-naphthyl)-N'-(o-isopropylphenyl)guanidine (940 mg, 44%) as white crystals. mp 175°-177° C.

IR ($CHCl_3$): 1650, 3400 and 3500 cm$^{-1}$.

$^1$H NMR ($CDCl_3$): δ 1.22 (d, 6H, J=6.6 Hz), 3.28-3.32 (m, 1H) and 7.16-8.19 (m, 11H)

Anal. Calcd for $C_{20}H_{21}N_3$: C, 79.17; H, 6.98; N, 13.85. Found: C, 78.92: H, 7.08; N, 13.77.

EXAMPLE 8

Radioligand Binding Assays

PCP receptor binding assays were performed using rat brain membranes as the source of receptors. The radioligand used to label PCP receptors was [$^3$H]MK-801 (97 Ci/mmol).

Synthesis of [$^3$H]MK-801 and PCP receptor binding assay protocols are described in Keana, J. F. W., Scherz, M. W., Quarum, M., Sonders, M. S., and Weber, E., *Life Sci.* 43, 965-973 (1988). Briefly, in the protocols, rat brain membranes were prepared and used as described for "detergent-treated membranes" (see Murphy, D. E., Schneider, J., Boehm, C., Lehmann, J., and Williams, M., *J. Pharmacol. Exp. Ther.* 240. 778-784 (1987)), and stored at a protein concentration of 10 mg/ml at −70° C. No effect of storage (1 month) of the membranes at −70° C. on receptor number or affinity for [$^3$H]MK-801 was observed.

For assays with rat membranes, the thawed membranes were incubated at 1 mg/ml with 0.01% Triton X-100 for 15 minutes at 32° C., then washed three times by centrifugation to reduce the endogenous amino acid concentrations, and finally resuspended in buffer for assay. Glycine and 1-glutamate were each added back to a final concentration of 1 μM to maximally stimulate the [$^3$H]MK-801 binding. The assays contain 400 μl of membranes, 50 μl of radioligand, and 50 μl of buffer or unlabelled drug.

For [$^3$H]MK-801 binding, 1 nM radioligand was incubated with 200 μg/ml of rat brain membranes for 4 hours at room temperature. All assays were stopped by rapid filtration under vacuum through Whatman GF/B glass fiber filters presoaked in 0.05% polyethyleneimine using a Brandel 48-well cell harvester (Brandel, Gaithersburg, Md.). The filters were washed three times with 5 ml of cold 5 mM tris-HCl, pH=7.4. Each filter was suspended in 10 ml of Cytoscint (ICN Biomedicals, Costa Mesa, Calif.) and radioactivity was measured by liquid scintillation spectrometry at a counting efficiency of 50%. Nonspecific binding was defined as that remaining in the presence of 10 pM MK-801 or 100 μM PCP.

[$^3$H]CPP (3-((±)2-carboxy-piperazine-4-yl)-propyl-1-phosphonic acid) binding to the N-methyl-D-aspartate-type glutamate receptor (Murphy, D. E. et al., *J. Pharmacol. Exp. Ther.* 240:778-784(1987)), high affinity [$^3$H]kainate binding to the kainate-type glutamate receptor (Honore, T. et al., *Neurosci Lett.* 65: 47-52 (1986)), and [$^3$H]AMPA (DL-α-amino-3-hydroxy-5-methylisoxazole-4-propionic acid) binding to the quisaqualate-type glutamate receptor (Murphy, D. E., Snowhill, E. W., and Williams, M., *Neurochem. Res.* 12, 775-782 (1987)) were assayed using rat brain membranes prepared as described above.

Saturation data were evaluated and $IC_{50}$ values were determined as described by J. B. Fischer and A. Schonbrunn (J. Biol. Chem. 263, 2808-2816 (1988)).

The N,N'-disubstituted guanidines were tested for binding to the PCP receptor on rat brain membranes in radioligand binding assays using selective [$^3$H]-labelled ligands (+)[$^3$H]MK-801 was used to label PCP receptors. As can be seen in Table I, the N,N'-disubstituted guanidines had submicromolar affinities for PCP receptors as judged by their ability to displace the selective PCP receptor ligand from binding to brain membranes from rat. (The numbers in parentheses in Table I indicates the number of experiments.)

In contrast, none of the compounds tested showed significant binding affinity towards the N-methyl-D-aspartate-, kainate- or quisqualate-type glutamate binding sites, assayed using [$^3$H]CPP, [$^3$H]kainate and [$^3$H]AMPA, respectively, as specific radioligands.

TABLE I

| | $IC_{50}$ (nM) In Rat Brain Membranes vs. $^3$H-MK801 | | |
|---|---|---|---|
| Compound | MEAN | SEM | (n) |
| II | 216.7 | 23.4 | (9) |
| III | 407.2 | 50.9 | (5) |
| IV | 267.2 | 53.4 | (5) |
| V | 493.1 | 34.6 | (4) |
| VI | 209.1 | 49.7 | (4) |
| VII | 38.6 | 7.3 | (6) |
| VIII | 102.1 | 21.6 | (4) |

EXAMPLE 9

In Vitro Neurotoxicity Assay a. Cell culture: Dissociated rat hippocampal cultures were prepared using a modification of the method of Huettner and Baughman (Huettner, J. E. and Baughman, R. W., *J. Neurosci.* 6, 3044-3060 (1986)). Newborn to 1 day old rat pups weighing 6 to 8 g were anesthetized with chloral hydrate and cortices with hippocampi attached were removed and placed in Cl$^-$ free dissociation medium supplemented with 1 mM kynurenic acid and 10 mM $MgSO_4$ [Choi, D. W., J. Neurosci. 7:369-379 (1987)]. The tissue was cleared of meninges, washed and incubated for 20 min at 37° C. in dissociation medium containing 10 units/ml of Papain (Worthington). After the enzyme treatment, the tissue was incubated for three 5-minute periods at 37° C. with 10 mg/ml trypsin inhibitor (Sigma type II-0).

The cells were dissociated by trituration in growth medium and a 50 μl cell suspension was added to each well of 96 well microtiter plates (Falcon) containing 50 μl growth medium per well. Prior to use the 96 well plates had been coated with poly-D-lysine (0.5 mg/ml) and lamininn (2 ug/ml) (Collaborative Research). Cells were plated at a density of $5 \times 10^4$ per well to give a final volume of 100 μl per well. The growth medium was Eagle's minimum essential media (MEM, Earle's salts) supplemented with 5% fetal bovine serum (CCL), 5% defined supplemented calf serum (HyClone), 50 mM glucose, 50 units/ml penicillin/streptomycin and MITO+ serum extender (Collaborative Research). The cells were maintained at 37° C. in a humidified 4.5% $CO_2$ atmosphere. On culture day 3, proliferation of non-neuronal cells was arrested by adding 5 μM cytosine arabinoside.

The cells were maintained in a medium that was similar to the growth medium but without the fetal bovine serum. Half volume media exchanges were performed twice weekly until 15 to 16 days in vitro when cytotoxicity assays were performed.

b. Glutamate Induced Neurotoxicity/Lactate Dehydrogenase Assay: Cultures were assessed microscopically and only those plates with uniform neuronal densities were used in the glutamate neurotoxicity trials. Glutamate trials were carried out at room temperature with all solutions warmed to 37° C. Cultures were washed three times in a HEPES-buffered "control salt solution" (CSS) similar to that reported by Choi et al. in *J. Neurosci.* 7:257–268 (1987), but with 10 mM HEPES substituted for Tris-HCl and buffered for pH 7.4. Rapid media exchanges are achieved in this system through the use of a 96 well aspirator which removes medium from all wells simultaneously and leaves equal volumes of fluid in each well thereby achieving uniform drug concentrations and eliminating the risk of exposing the cells to air. Drugs are tested against 500 μM glutamate using multiple ½ fold dilutions (usually 7) of test substance to give a dose response curve and 3 controls which include 500 μM glutamate alone, test drug alone (highest concentration) and CSS alone. One 96 well plate is used per drug to give a sample size of 8 and trials are repeated several times. Following the CSS washes where all traces of serum containing media are removed, the cells are exposed for 5 minutes to the 7 concentrations of test drug in CSS and then to the same drug concentrations plus 500 μM glutamate. The three CSS washes are repeated and 100 μl aliquots of glucose-enriched MEM are added to all wells and the plates are maintained overnight at 37° C. in $CO_2$ incubator.

The glutamate-induced death of neurons is measured by determining the levels of lactate dehydrogenase (LDH, a cytosolic enzyme) released into the medium by dead and dying neurons in the 24–48 hours following glutamate insult as described by Koh and Choi (*J. Neurosci. Methods* 20:83–90 (1987)). It has also been established that non-neuronal cells, such as astrocytes, do not release significant levels of LDH during these trials. Media samples are collected from all wells and assayed for LDH according to the protocol suggested by Molecular Devices Applications Bulletin, 012-A using the Molecular Devices Kinetic Microplate Reader. Results are normalized to the LDH values obtained in the glutamate alone controls.

A measure of the potency of each compound tested is made by estimating from the dose-response curve, the concentration of the compound that inhibits 50% of the glutamate-induced LDH release. This estimate is called the $ED_{50}$ dose.

Figure 1:
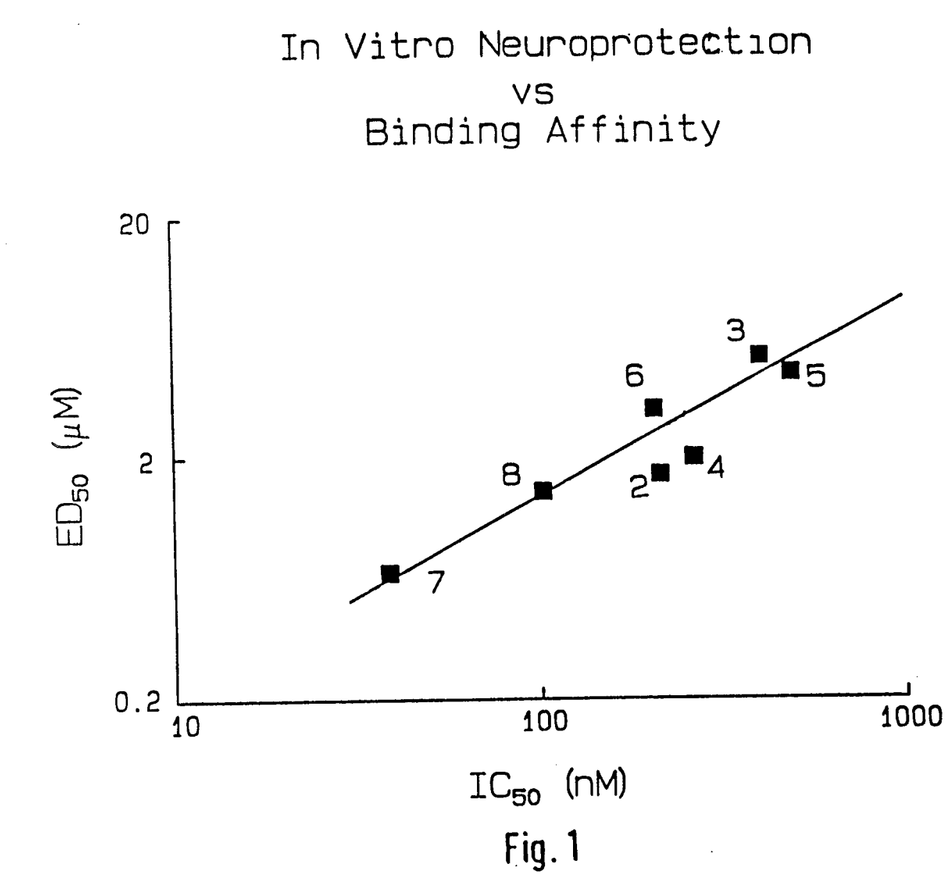
FIG. 1 is a graphical comparison of the data resulting from the in vitro neurotoxicity assay with the data resulting from the radioligand binding assay for the compounds which are given as examples and which are the subject of the claims.

All of the disubstituted guanidines tested were able to inhibit glutamate-induced neurotoxicity in vitro. FIG. 1 shows the relationship between $ED_{50}$ values and $IC_{50}$ values for the compounds II–VIII (denoted as the corresponding numbers 2–8). The neuroprotective potencies of the compounds are closely correlated to their affinities for the PCP receptor.

The disubstituted guanidines of the present invention are chemically unrelated to any known NMDA channel blockers acting through PCP receptors. As discussed above, previously, only compounds belonging to the PCP/ketamine series, benzomorphan opiates, benz-f-isoquinolines and MK-801 were known to interact with PCP receptors.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A neuroprotecting symmetrical N,N'-disubstituted guanidine which exhibits a high binding activity with respect to the PCP receptor in the NMDA receptor-channel complex and is selected from the group consisting of bis-1,3-(o-isopropylphenyl)guanidine, bis-1,3-(m-isopropylphenyl)guanidine, and bis-1,3-(m-methoxyphenyl)guanidine; or a physiologically acceptable salt thereof.

2. Bis-1,3-(o-isopropylphenyl)guanidine.

3. Bis-1,3-(m-isopropylphenyl)guanidine.

4. Bis-1,3-(m-methoxyphenyl)guanidine.

5. A neuroprotecting asymmetrical N,N'-disubstituted guanidine which exhibits a high binding activity with respect to the PCP receptor in the NMDA receptor-channel complex and is selected from the group consisting of N-(1-naphthyl)-N'-(o-iodophenyl)guanidine, N-(1-naphthyl)-N'-(m-ethylphenyl)guanidine, and N-(1-naphthyl)-N'-(o-isopropylphenyl)guanidine; or a physiologically acceptable salt thereof.

6. N-(1-naphthyl)-N'-(o-iodophenyl)guanidine.

7. N-(1-naphthyl)-N'-(m-ethylphenyl)guanidine.

8. N-(1-naphthyl)-N'-(o-isopropylphenyl)-guanidine.

9. A method of inhibiting NMDA receptor-ion channel related neurotoxicity in a mammal exhibiting such neurotoxicity or susceptible thereto, comprising administering to the mammal a symmetrical N,N'-disubstituted guanidine selected from the group consisting of bis-1,3-(o-isopropylphenyl)guanidine, bis-1,3-(m-isopropylphenyl)guanidine, bis-1,3-(1-naphthyl)guanidine and bis-1,3-(m-methoxyphenyl)guanidine; or a physiologically acceptable salt thereof; wherein said N,N'-disubstituted guanidine possesses a high affinity for the PCP receptor of a nerve cell, and wherein said N,N'-disubstituted guanidine is administered in an amount effective to inhibit the neurotoxicity.

10. The method according to claim 9, wherein said neurotoxicity is caused by excessive release of endogenous glutamate following the occurrence of hypoxia, hypoglycemia, brain or spinal chord ischemia, or brain or spinal cord trauma.

11. The method according to claim 10, wherein said N,N'-disubstituted guanidine is bis-1,3-(o-isopropylphenyl)guanidine.

12. The method according to claim 10, wherein said N,N'-disubstituted guanidine is bis-1,3-(m-isopropylphenyl)guanidine.

13. The method according to claim 10, wherein said N,N'-disubstituted guanidine is bis-1,3-(1-naphthyl)-guanidine.

14. The method according to claim 10, wherein said N,N'-disubstituted guanidine is bis-1,3-(m-methoxyphenyl)guanidine.

15. A method of inhibiting NMDA receptor-ion channel related neurotoxicity in a mammal exhibiting such neurotoxicity or susceptible thereto, comprising administering to the mammal exhibiting such neurotoxicity or susceptible thereto an asymmetrical N,N'-disubstituted guanidine possessing a high affinity for the PCP receptor of a nerve cell, in an amount effective to inhibit the neurotoxicity.

16. The method according to claim 15, wherein said neurotoxicity is caused by excessive release of endogenous glutamate following the occurrence of hypoxia, hypoglycemia, brain or spinal chord ischemia, or brain or spinal cord trauma.

17. The method according to claim 16, wherein the asymmetrical N,N'-disubstituted guanidine is selected from the group consisting of N-(1-naphthyl)-N'-(o-iodophenyl)guanidine, N-(1-naphthyl)-N'-(m-ethylphenyl)guanidine, and N-(1-naphthyl)-N'-(o-isopropylphenyl)guanidine; or a physiologically acceptable salt thereof.

18. The method according to claim 17, wherein the asymmetrical N,N'-disubstituted guanidine is N-(1-naphthyl)-N'-(o-iodophenyl)-guanidine.

19. The method according to claim 18, wherein the asymmetrical N,N'-disubstituted guanidine is N-(1-naphthyl)-N'-(m-ethylphenyl)guanidine.

20. The method according to claim 18, wherein the asymmetrical N,N'-disubstituted guanidine is N-(1-naphthyl)-N'-(o-isopropylphenyl)guanidine.

21. A method for treating a disease of the nervous system in which the pathophysiology of the disorder involves excessive excitation of nerve cells by agonists of NMDA receptors comprising the administration to a mammal exhibiting symptoms of such disorders or susceptible to such disorders, a symmetrical N,N'-disubstituted guanidine selected from the group consisting of bis-1,3-(o-isopropylphenyl)guanidine, bis-1,3-(m-isopropylphenyl)guanidine, bis-1,3-(1-naphthyl)guanidine and bis 1,3-(m-methoxyphenyl)guanidine; or a physiologically acceptable salt thereof; wherein said symmetrical N,N'-disubstituted guanidine has a high affinity for the PCP receptor of the nerve cell, and said guanidine is administered in an amount effective to treat said disease.

22. The method of claim 21, wherein said N,N'-disubstituted guanidine is bis-1,3-(o-isopropylphenyl)guanidine.

23. The method of claim 22, wherein said N,N'-disubstituted guanidine is bis-1,3-(m-isopropylphenyl)guanidine.

24. The method of claim 22, wherein said N,N'-disubstituted guanidine is bis-1,3-(1-naphthyl)guanidine.

25. The method of claim 22, wherein said N,N'-disubstituted guanidine is bis-1,3-(m-methoxyphenyl)guanidine.

26. A method for treating a disease of the nervous system in which the pathophysiology of the disorder involves excessive excitation of nerve cells by agonists of NMDA receptors comprising the administration to a mammal exhibiting symptoms of such disorders or is susceptible to such disorders, an asymmetrical N,N'-disubstituted guanidine having a high affinity for the PCP receptor of the NMDA receptor-channel complex, in an amount effective to treat said disease.

27. The method according to claim 26, said asymmetrical N,N'-disubstituted guanidine having the formula wherein R and R' are different and are an alkyl group of 4–12 carbon atoms, a cycloalkyl group of 3–12 carbon atoms, carbocyclic aryl, alkaryl, aralkyl or heterocyclic groups of 6–18 carbon atoms and containing 1–3 separate or fused rings.

28. The method according to claim 27, wherein the asymmetrical N,N'-disubstituted guanidine is selected from the group consisting of N-(1-naphthyl)-N'-(o-iodophenyl)guanidine, N-(1-naphthyl)-N'-(m-ethylphenyl)guanidine, and N-(1-naphthyl)-N'-(o-isopropylphenyl)guanidine; or a physiologically acceptable salt thereof.

29. The method according to claim 28, wherein said asymmetrical N,N'-disubstituted guanidine is N-(1-naphthyl)-N'-(o-iodophenyl)guanidine.

30. The method according to claim 29, wherein said asymmetrical N,N'-disubstituted guanidine is N-(1-naphthyl)-N'-(m-ethylphenyl)guanidine.

31. The method according to claim 29, wherein said asymmetrical N,N'-disubstituted guanidine is N-(1-naphthyl)-N'-(o-isopropylphenyl)guanidine.

32. The method according to claim 22, wherein said disease is Alzheimer's disease, Huntington's disease, Amyotrophic Lateral Sclerosis, Down's Syndrome or Korsakoff's disease.

33. The method according to claim 32, wherein said N,N'-disubstituted guanidine is bis-1,3-(o-isopropylphenyl)guanidine.

34. The method according to claim 33, wherein said N,N'-disubstituted guanidine is bis-1,3-(m-isopropylphenyl)guanidine.

35. The method according to claim 33, wherein said N,N'-disubstituted guanidine is bis-1,3-(1-naphthyl)-guanidine.

36. The method according to claim 33, wherein said N,N'-disubstituted guanidine is bis-1,3-(m-methoxyphenyl)guanidine.

37. The method according to claim 27, wherein said disease is Alzheimer's disease, Huntington's disease, Amyotrophic Lateral Sclerosis, Down's Syndrome or Korsakoff's disease.

38. The method according to claim 37, wherein the asymmetrical N,N'-disubstituted guanidine is selected from the group consisting of N-(1-naphthyl)-N'-(o-iodophenyl)guanidine, N-(1-naphthyl)-N'-(m-ethylphenyl)guanidine, and N-(1-naphthyl)-N'-(o-isopropylphenyl)guanidine; or a physiologically acceptable salt thereof.

39. The method according to claim 38, wherein the asymmetrical N,N'-disubstituted guanidine is N-(1-naphthyl)-N'-(o-iodophenyl)-guanidine.

40. The method according to claim 39, wherein the asymmetrical N,N'-disubstituted guanidine is N-(1-naphthyl)-N'-(m-ethylphenyl)guanidine.

41. The method according to claim 39, wherein said asymmetrical N,N'-disubstituted guanidine is N-(1-naphthyl)-N'-(o-isopropylphenyl)guanidine.

42. The method according to claim 22, wherein the mammal is a human being suffering from epilepsy.

43. The method of claim 42, wherein said N,N'-disubstituted guanidine is bis-1,3-(o-isopropylphenyl)guanidine.

44. The method of claim 43, wherein said N,N'-disubstituted guanidine is bis-1,3-(m-isopropylphenyl)guanidine.

45. The method of claim 43, wherein said N,N'-disubstituted guanidine is bis-1,3-(1-naphthyl)guanidine.

46. The method of claim 43, wherein said N,N'-disubstituted guanidine is bis-1,3-(m-methoxyphenyl)guanidine.

47. The method according to claim 27, wherein the mammal is a human being suffering from epilepsy.

48. The method according to claim 47, wherein the asymmetrical N,N'-disubstituted guanidine is selected from the group consisting of N-(1-naphthyl)-N'-(o-iodophenyl)guanidine, N-(1-naphthyl)-N'-(m-ethylphenyl)guanidine, and N-(1-naphthyl)-N'-(o-isopropylphenyl)guanidine; or a physiologically acceptable salt thereof.

49. The method according to claim 48, wherein the asymmetrical N,N-disubstituted guanidine is N-(1-naphthyl)-N'-(o-iodophenyl)guanidine.

50. The method according to claim 49, wherein the asymmetrical N,N'-disubstituted guanidine is N-(1-naphthyl)-N'-(m-ethylphenyl)guanidine.

51. The method according to claim 49, wherein the asymmetrical N,N'-disubstituted guanidine is N-(1-naphthyl)-N'-(o-isopropylphenyl)guanidine.

* * * * *